US005649970A

United States Patent [19]
Loeb et al.

[11] Patent Number: 5,649,970
[45] Date of Patent: Jul. 22, 1997

[54] EDGE-EFFECT ELECTRODES FOR INDUCING SPATIALLY CONTROLLED DISTRIBUTIONS OF ELECTRICAL POTENTIALS IN VOLUME CONDUCTIVE MEDIA

[76] Inventors: Gerald E. Loeb, 90 Bagot Street, Kingston, Ontario, Canada, K7L 3E5; Helen Ruddy, 35 Rudd Ave., Kingston, Ont, Canada, K7L 4V1

[21] Appl. No.: 516,758

[22] Filed: Aug. 18, 1995

[51] Int. Cl.⁶ .................................................. A61N 1/36
[52] U.S. Cl. ........................... 607/57; 607/67; 607/72; 607/116; 607/137
[58] Field of Search ........................... 607/55–58, 67, 607/72, 115, 116, 119, 122, 123, 125, 136, 137

[56] References Cited

U.S. PATENT DOCUMENTS

| | | | |
|---|---|---|---|
| 3,449,768 | 6/1969 | Doyle . | |
| 4,686,765 | 8/1987 | Byers et al. | 29/858 |
| 4,819,647 | 4/1989 | Byers et al. | 128/642 |
| 4,832,051 | 5/1989 | Jarvik et al. | 607/116 |
| 4,907,601 | 3/1990 | Frick | 607/72 |
| 4,969,468 | 11/1990 | Byers et al. | 607/118 |
| 5,181,511 | 1/1993 | Nickolls et al. | 607/4 |
| 5,405,375 | 4/1995 | Ayers et al. | 607/122 |
| 5,531,774 | 7/1996 | Schulman et al. | 607/56 |

OTHER PUBLICATIONS

Medical and Biological Engineering, vol. 12, No. 1, pp. 131–135, 607/116. Jan. 1974.
Loeb et al., "Design and Fabrication of an Experimental Cochlear Prosthesis", Medical & Biological Engineering & Computing, vol. 21, pp. 241–254, 607/056. May 1983.

*Primary Examiner*—Jeffrey R. Jastrzab
*Attorney, Agent, or Firm*—Fitch, Even, Tabin & Flannery

[57] ABSTRACT

An electrode array for implantation in volume-conductive media, such as living tissue, includes at least two closely spaced metal contacts, with arbitrary shapes, having large enough surface areas to preclude one or both from acting as a "point source." Through proper control of the shape of the contacts, and the impedance ratio between the metal-electrolyte interface and the intervening volume-conductive media, achieved through use of appropriate materials for the metal contacts in combination with electronic adjustment of the voltage pulse applied between the contacts, desirable "edge-effect" fields are created that better control and manage the distribution of the resulting stimulation current flowing between the contacts. Such control of the stimulation current distribution allows a given electrode array to be electronically tuned to better stimulate specific neurons found within the tissue. One embodiment of the electrode array includes a plurality of single, relatively small, contacts, each having its own lead attached thereto, that lie in close proximity to a highly elongated contact, having a single lead attached thereto. When an electrical potential pulse is applied between a given one of the small contacts and the elongate contact, most of the current flow through the elongated contact occurs in a small region on its surface immediately adjacent to the nearby contact. In such embodiment, N perpendicular bipolar fields are thus created using only N+1 leads.

22 Claims, 5 Drawing Sheets

EDGE-EFFECT ELECTRODES FOR INDUCING SPATIALLY CONTROLLED DISTRIBUTIONS OF ELECTRICAL POTENTIALS IN VOLUME CONDUCTIVE MEDIA

BACKGROUND OF THE INVENTION

The present invention relates to functional electrical stimulation (FES), and more particularly to edge-effect electrodes, and a method of using edge-effect electrodes, to better control the location of electrical stimulation within volume conductive media.

Many FES applications require that an electrical stimulation pulse be applied to a precise tissue or neural location. Heretofore, such precise positioning has been attempted through the manufacture of precision electrodes that are carefully implanted to contact conductive media (tissue and/or nerves) at the exact location where the stimulation is desired. Problematically, it is not always possible to make electrodes of an appropriate size and tolerance, nor to position such electrodes at an appropriate implant location, so as to force the electrical stimulation to occur at the precise media location. What is needed, therefore, is an electrode, or electrode array, and a method of using such electrode or electrode array, that does not require precision tolerances during manufacture, does not necessitate precise positioning during implantation, and yet still allows an electrical stimulation pulse to be precisely guided to a desired conductive media location.

The configuration of electrode contacts used for stimulation is usually divided into unipolar and bipolar. In unipolar stimulation, electrical current is applied to the surrounding media by a circuit consisting of an active contact or electrode placed close to the target of the stimulation and an indifferent (or common) contact or electrode that is remote from the target. The indifferent electrode usually has a large surface area. Unipolar stimulation produces electrical fields whose distributions of gradients in the surrounding conductive media (e.g., body tissue and fluids) are not precise, causing current flow through the conductive media that is difficult to direct to a small target volume within the media.

When more confined or specifically oriented field gradients are desired, bipolar electrodes are usually employed. Bipolar electrodes apply electrical currents via a pair of closely spaced contacts (electrodes). By positioning the pair of electrodes so that the target volume is adjacent or inbetween the pair of electrodes, more precise electrical stimulation is achieved. For example, in a cochlear prosthesis, it is desirable to have a closely spaced series of channels, each of which produces a field gradient oriented perpendicularly to the axis separating the channels so as to selectively recruit the auditory neurons whose processes lie similarly perpendicularly to the axis of the channels along the length of the cochlear spiral. See, e.g., U.S. Pat. No. 4,819,647. Such a configuration requires two separate contacts and their associated leads for each channel of stimulation. Thus, if N channels are employed, 2N leads are required, one for each electrode of each bipolar pair of electrodes.

The actual distribution of field gradients associated with a bipolar pair of electrodes, which distribution controls the selectivity of each electrode site, is fixed by the electrode geometry and cannot be varied by electronic means. It would be desirable for many FES applications, including multi-channel intra-cochlear prosthesis applications, to increase the number of channels and to modulate the selectivity of each channel to take advantage of conditions that may be unique to each patient. Unfortunately, however, for many FES applications, including the use of a multichannel intra-cochlear prosthesis to restore hearing in certain cases of sensorineural deafness, it is impractical to add more separate contacts and leads due to the small and complex geometry associated with the target conductive media. What is needed, therefore, is an electrode array that provides additional bipolar channels for use with small and complex geometries, such as encountered in the cochlea/auditory nerve interface, without unduly increasing the number of leads required.

An electrode array is shown in U.S. Pat. No. 3,449,768 that utilizes a plurality of point electrodes and a single spiral reference electrode disposed within an insulative carrier. The single spiral reference electrode is coiled or wound within the carrier so as to have respective portions thereof exposed near each of the point electrodes. Such construction thus attempts to effectively place separate reference electrodes, commonly connected, at differing locations along the length of the array. As such, the electrode geometry is fixed, and the distribution of field gradients associated with a given pair of electrodes, i.e., associated with one of the point electrodes and the closest exposed reference electrode, is also effectively fixed, and there is no effective way to control the field distribution by electronic means. Hence, what is needed is an electrode array where the electric field distribution may be controlled in an appropriate manner by electronic means.

SUMMARY OF THE INVENTION

The present invention addresses the above and other needs through the use of edge-effect electrodes, typically configured in an electrode array, in combination with an appropriate implantable stimulator device that applies a controlled potential to the edge-effect electrodes. An edge-effect electrode, for purposes of the present application, is one that is sufficiently large so that it does not function as a point contact, i.e., an electrode whereon the current density across its surface is not uniform, but varies as a function of the metal-electrode interface with the conductive media at any given point along the edge or surface of the electrode. Thus, for example, the current density associated with an edge effect electrode may be highest at a particular region along its surface or edge where a field gradient associated with an applied electric field is highest. This allows the spatial current density in the conductive media surrounding the electrode(s) to be effectively steered or guided by the selective application and control of an electric field between the electrodes. This means that the electrodes need not be positioned within the body tissue with the same degree of exactness and precision as has heretofore been required because to a certain extent the effective position of the electrodes can be electronically tuned. It also means that much more flexibility with respect to stimulation patterns and stimulation locations within the body tissue is achievable than has previously been possible.

It is noted that edge effects of electrodes have been recognized previously in the art; however, heretofore, such effects have been viewed as a problem to be avoided in order to prevent high current densities which might otherwise damage sensitive body tissue and/or accelerate electrode corrosion. Hence, specific electrode configurations, e.g., feathered edges, and specific electrode materials, e.g., Sagi-Dolev, et al., 1992, have been used in the prior art in order to prevent edge effects from occurring. Advantageously, the present invention recognizes that such anti-edge-effect measures need not be utilized, but rather allows the electrodes to be designed and built so that edge effects are deliberately obtained.

The desired controllable current density of an edge-effect electrode made in accordance with the present invention requires that a very low impedance be maintained at the interface between the metal electrode surface and the surrounding conductive media, e.g., body tissue. Such requirement, in turn, necessitates that the electrode(s) be made from specific materials. Hence, in accordance with one aspect of the invention, the edge-effect electrodes are fabricated to have a much lower impedance than has heretofore been achievable. More particularly, the electrodes are fabricated from iridium metal, which can be electrochemically activated so as to reduce its interfacial impedance by a factor of 10 or more below that achievable with inactive iridium or other metals. The effect of using low impedance electrodes in this fashion is that the gradients of the current density may be controlled, not just by the relative spacing between the electrodes, but also by the frequency content of the stimulation current pulses. In other words, the electrodes of the present invention allow the distribution of the current density gradients to be controlled, to a certain extent, through electronic means.

In accordance with another aspect of the invention, an electrode array, and method of designing an electrode array, is provided that allows closely spaced nerves or groups of neurons to be selectively and independently stimulated in bipolar fashion without the need for separate electrical contacts and corresponding leads for each stimulated location. Such an electrode array includes a plurality of single, small, contacts held in a resilient carrier that may be shaped to fit the medium wherein the array is to be inserted or implanted. Each single contact has a lead associated therewith that allows independent electrical contact to be made therewith. The single small contacts lie in close proximity to a highly elongated edge-effect contact, also held by the resilient carrier. The elongated contact is exposed along its entire length. A single lead connects to the elongated contact at one end to allow electrical contact to be made therewith.

In use, an electrical potential is applied between the elongated contact and a desired single contact where stimulation is desired in order to energize such contacts. As a result of such energization, an electrical field, and associated gradient distribution, is created between the elongated contact and the energized single contact. Such electrical field causes an electrical stimulating current to flow between the energized single contact and the elongated contact. Almost all of the current flow through the elongated contact occurs in a small region on its surface immediately adjacent the nearby single contact, where the field gradient is the strongest. Thus, the elongated contact in combination with the energized single contact function effectively as a bipolar pair of contacts. Thus, N perpendicular bipolar fields are created using only N+1 leads instead of the 2N leads typically required by discrete pairs of bipolar electrodes. Further, the distribution of field gradients associated with the resulting "bipolar" pair of electrodes can be varied, within certain limits, by electronic means, e.g., by adjusting the magnitude of the applied electrical potential, and the frequency content of the stimulation current pulses.

In accordance with yet another aspect of the invention, it is possible to create an arbitrary number of "virtual dipoles" that are oriented perpendicularly to the elongated contact but located in positions that are intermediate between the other available contacts. This is done by connecting two such small single contacts together in such a way that they each inject a portion of the total current that is returned through the elongated contact. The fields that would be produced by each small contact alone thus combine linearly to produce a net dipole that is directed perpendicularly to a long axis of the elongated contact. The exact location of the "virtual dipoles" is controllable by controlling the magnitude of the applied electrical potential to each of the small single contacts, thereby controlling the amount of current that each injects. Hence, using such electrode array, electronic means may be used to control, within certain limits, the distribution of the current density gradients.

An electrode array made as described thus advantageously provides one or more narrowly focussed, temporospatial patterns of activation in conductive media, such as the nervous system. The array is particularly suited for small geometries where an array of several "bipolar" electrodes is needed, but where there is insufficient space for the 2N electrode wires that must typically be used with a bipolar electrode array of N electrodes. For example, the array is particularly suited for insertion into the cochlea as part of a multichannel cochlear prosthesis.

It is thus a feature of the invention to provide edge-effect electrodes for use in FES and related applications.

It is another feature of the invention to provide an array of electrodes suitable for implantation in living tissue or other conductive media that promote edge effects to allow the current density associated with the electrode/media interface to be controlled and steered.

It is an additional feature of the invention, in accordance with one embodiment thereof, to provide a passive implantable electrode array for use in functional electrical stimulation (FES) applications that effectively provides bipolar stimulation for N narrowly focussed stimulation sites, while only requiring N+1 electrical leads connected thereto.

It is a further feature of the invention to provide such an electrode array that is small, flexible and compact, and that is particularly suited for implantation in very tight quarters or small volumes, such as within the cochlea.

It is another feature of the invention to provide such an electrode array wherein the gradients of the stimulation current density achieved by such array are controllable, in part, by electronic means, and in part by the geometry of the array and the materials from which the electrodes of the array are made.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
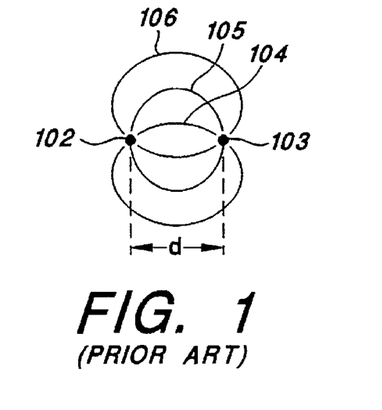
FIG. 1 shows a pair of point electrodes in a classical dipole electrode configuration, and further illustrates the electric field gradients that result when an electric potential is applied between the electrodes.

Turning first to FIG. 1, there is shown a pair of point electrodes 102, 103 in a classical dipole electrode configuration, separated a distance d from each other. When an electric potential is applied between the point electrodes 102, 103, an electric field is established between the electrodes, which electric field is symbolically represented in FIG. 1 by the field gradient lines 104, 105, 106. The shorter the gradient line, the sharper and stronger the field. Thus, the gradient line 104 represents a relatively stronger field than does the gradient line 105. Similarly, the gradient line 105 represents a relatively stronger field than does the gradient line 106.

The separation distance d between the electrodes is typically referred to as the "dipole" distance. The dipole distance, or length of the dipole, provides a convenient measure for defining a "near field" and a "far field". A near field is generally considered as any field that is less than or equal to the length of the dipole. Conversely, a far field is a field that is greater than the length of the dipole. The most effective stimulation occurs in a near field, but it is not always possible to position the electrodes so that the desired neurons, or other tissue, lie within the near field. Hence, it would be desirable if the field of the dipole could be electronically "tuned" or "adjusted" so that a near field could be realized that encompassed the desired neurons or tissue to be stimulated, and that far field conditions would obtain for neurons or tissue whose stimulation is not desired.

When point electrodes are used, as modeled in FIG. 1, it is assumed that there are no edge effects, and that the current density across the surface of the electrodes is the same everywhere. When such conditions exist, there is no effective adjustment or tuning of the near/far field that can take place. A change in the amplitude or waveform of the applied electrical potential affects all parts of the field equally. The present invention, in contrast, recognizes that edge effects can be beneficial, and as a result, uses at least one electrode that is sufficiently large so as not to function as "point" electrode. With a non-point electrode, it therefore becomes possible to rely on the edge effects of the electrode to throw the near field over a larger or smaller area, and thereby better encompass a tissue/neuron area where stimulation is desired. Further, the deliberate use of edge effects allows the near field to be systematically controlled so that it moves or "slides" along a given stimulation region, without gaps in the near field coverage. Hence, stimulation can occur in the desired region without experiencing stimulation gaps.

The present invention thus includes an electrode array adapted for implantation in volume-conductive media, such as living tissue. Such array includes at least two closely spaced bipolar metal contacts, with arbitrary shapes, having large enough surface areas to preclude one or both from acting as a "point source" or "point electrode". Through proper control of the shape of the contacts, and the impedance ratio between the metal-electrolyte interface and the intervening volume-conductive media, achieved through use of appropriate materials for the metal contacts in combination with electronic adjustment of the voltage pulse applied between the contacts, desirable "edge-effect" fields are created that better control and manage the distribution of the resulting stimulation current flowing between the contacts. Such control of the stimulation current distribution, in turn, allows a given electrode array to be electronically tuned to better stimulate specific neurons found within the tissue.

The actual distribution of current density through the metal-electrolyte interface of a given electrode contact and the surrounding volume-conductive media depends on three factors: (1) the relative conductivity of the interfaces and the media; (2) the geometry of the interfaces and the electrical paths available through the media; and (3) the frequency content of the stimulation pulses (assuming that either or both of the interfacial and media conductivities contain frequency-dependent, reactive terms such as capacitance, which is usually the case). Such distribution may be expressed in terms of an equivalent dipole consisting of appropriately located point sources and sinks of current.

Stimulating electrodes of the prior art utilize electrical contacts having high impedances (low conductivities) relative to the media with which they come in contact. Hence, the only relevant geometrical factor that plays a meaningful role in the stimulation process is the relative spacing of the electrical contacts. Thus, because reactive terms only appear at the contact interfaces (the conductive media comprising essentially pure resistivities), the shape and frequency content of stimulation pulses of the prior art (applied electric potentials) are ignored.

In contrast, in one embodiment of the present invention, the stimulating electrodes are made from iridium metal. Such metal is electrochemically activated using techniques known in the art. Once activated, the interfacial impedance is reduced by a factor or ten or more below that achievable with inactive iridium or other metals. As a result, the gradients of current density achievable with such electrodes not only depend critically on the distances between different regions on the surfaces of two closely spaced contacts, but also on the frequency content (which includes the shape) of the stimulation pulse. In another embodiment of the invention, a similar effect on interfaced impedance is obtained with more conventional metals, such as platinum, by increasing the surface area of the contact without changing its geometric dimensions, accomplished by producing a rough texture of the surface of the contact.

Yet another embodiment employs at least some electrodes made from sintered particulate tantalum metal which results in a rough texture with a large effective surface area. Tantalum may be anodized electrochemically to produce a coating of tantalum pentoxide, which prevents corrosion of the tantalum.

Figure 2:
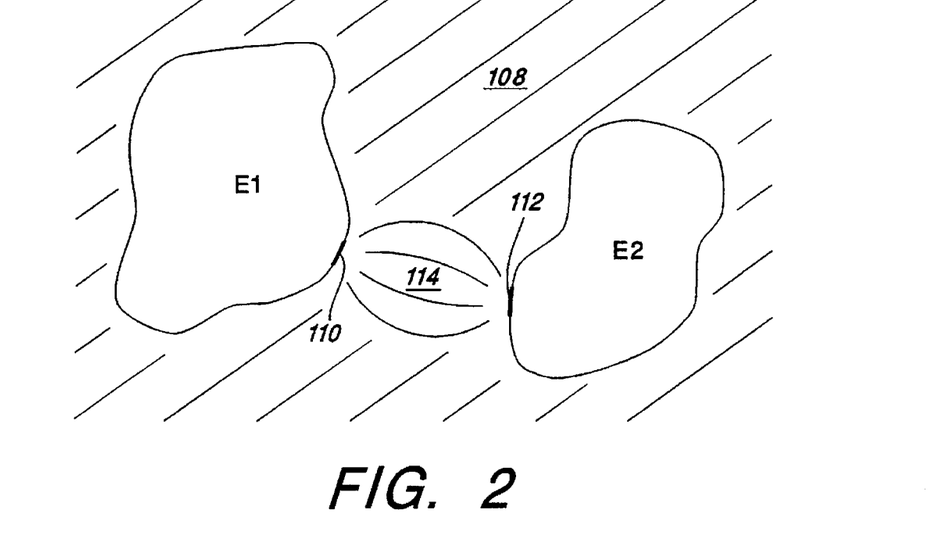
FIG. 2 generically depicts two edge-effect electrodes.

A pair of non-point electrodes E1 and E2 of the type that may be used with the present invention are symbolically represented in FIG. 2. The electrodes E1 and E2 are shown immersed in, or in contact with, conductive media 108. The shape of the electrodes E1 and E2 is arbitrary. The electrodes are made from or coated with an appropriate material, e.g., activated iridium, so that at least some regions along the interface between the surface of the electrodes and the media 108 represent a very low impedance. When an electric potential, e.g., a pulse, is applied between the electrodes, a near field 114 is created between selected edge regions 110 and 112 of the two electrodes, which near field 114 allows the current density in the near field region to be much greater than elsewhere within the conductive media. As a result, a much more localized stimulation is achieved within the media. Further, as explained below, by using appropriate combinations and groupings of electrodes, it is possible to move the near field around within the media 108, thereby effectively directing the stimulation to desired zones or regions within the media.

Figure 3:
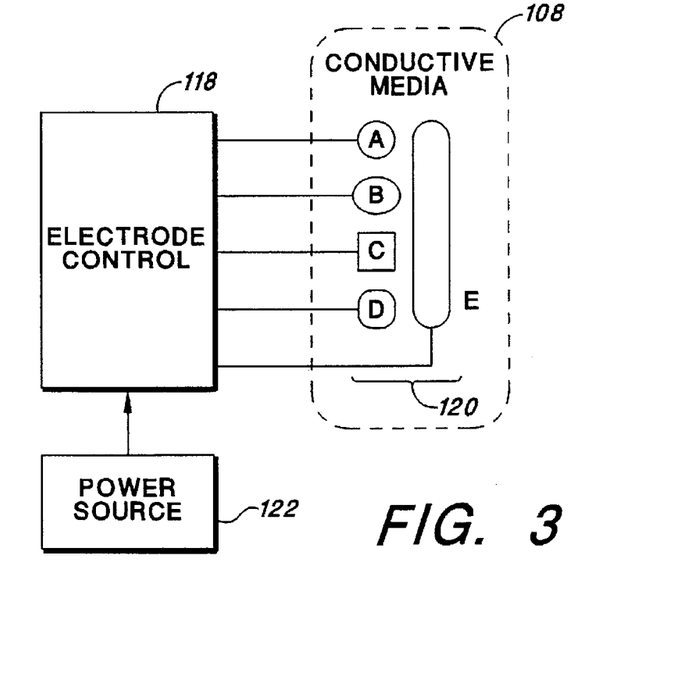
FIG. 3 illustrates a multiplicity of edge-effect electrodes arranged in an electrode array which is implanted in volume conductive media, and wherein electrical stimulation of the media through selected groupings of the electrodes is controlled through an electrode control circuit.

Turning next to FIG. 3, a representative electrode array 120 is shown immersed within volume conductive media 108. The array 120 includes five separate electrodes, labeled A, B, C, D and E. The use of five electrodes is only exemplary, as any number of electrodes could be employed. Each of the five electrodes is selectively connected to a power source 122 through an electrode control circuit 118. Three of the electrodes, electrodes A, B and D, are illustrated as being essentially round electrodes, while electrode C is depicted as a rectangular electrode, and electrode E is shown as an elongate electrode. Such shapes are not meant to be limiting, but merely suggest that the individual shape of the electrodes used with the present invention can assume almost any shape suited for the particular stimulation application at hand.

Figure 4A:
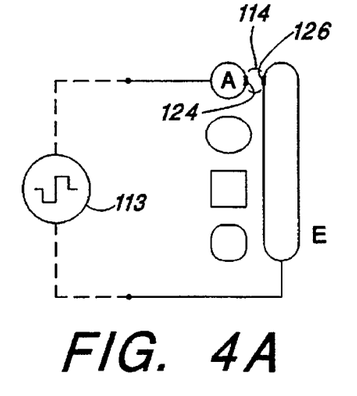
FIGS. 4A–4H depict some of the electrode groupings that may be used in accordance with the present invention to control the distribution of electrical stimulation in the media for the array shown in FIG. 3.
Figure 4B:
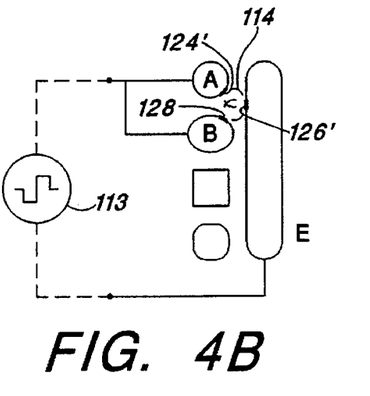

To illustrate how the electrode array 120 shown in FIG. 3 may be used, reference is next made to FIGS. 4A through 4H. These figures show representative stimulation configurations that could be employed by the electrode control circuit 118 (FIG. 3) in order to move the near field 114 around within the conductive media 108. In FIG. 4A, for example, an electric potential 113 is applied between electrodes A and E, which effectively positions the near field 114 between an edge portion 124 of electrode A, and another edge portion 126 of elongate electrode E. In FIG. 4B, in contrast, the electric potential is applied to electrodes A and B, electrically connected together, and the elongate electrode E. As a result, the near field 114 exists between an edge portion 124' of electrode A and an edge portion 126' of electrode E; as well as between an edge portion 128 of electrode B and the edge portion 126' of electrode E. Note that the edge portion 126' of electrode E in FIG. 4B has shifted slightly from the edge portion 126 shown in FIG. 4A, thereby allowing the stimulation current to also shift slightly.

Figure 4C:
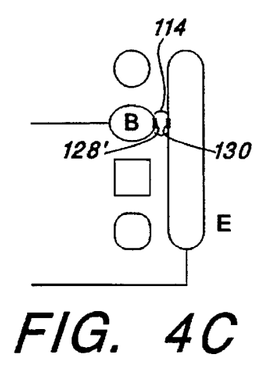
Figure 4D:
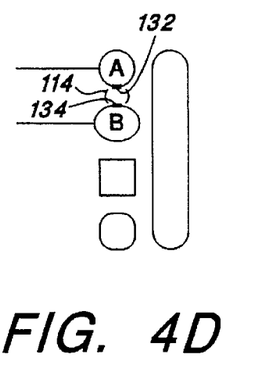
Figure 4E:
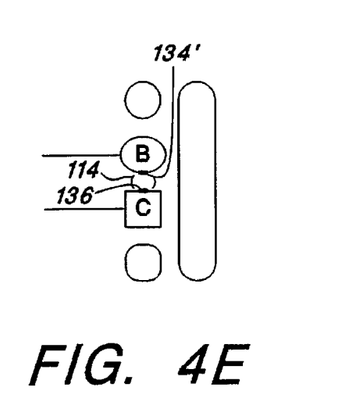
Figure 4F:
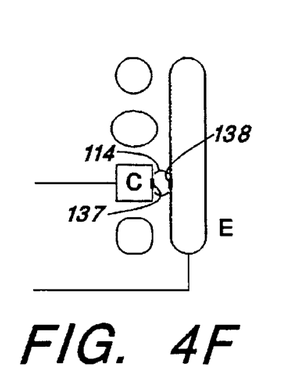

In FIG. 4C, the electric potential is applied between electrodes B and E, causing the near field 114 to exist in the area between an edge portion 128' of electrode B, and an edge portion 130 of electrode E. In FIG. 4D, the potential is applied between electrodes A and B, moving the near field 114 between fronting edge portions 132 and 134 of the electrodes A and B. In FIG. 4E, the potential is applied between electrodes B and C, thereby placing the near field 114 between fronting edge portions 134' and 136 of the electrodes B and C. In a similar manner, in FIG. 4F, the potential is applied between electrodes C and E, forcing the near field 114 to be established between an edge portion 137 of electrode C, and a fronting edge portion 138 of electrode E.

Figure 4G:
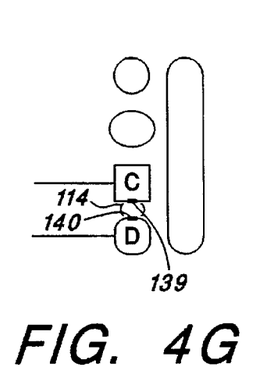
Figure 4H:
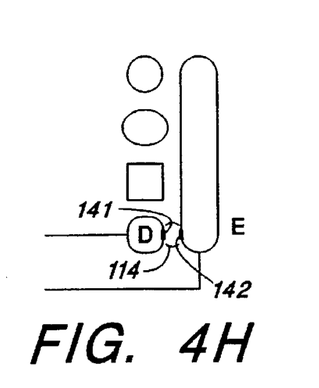

In FIG. 4G, the potential is applied between electrodes C and D, which causes the near field 114 to move to the region between an edge portion 139 of electrode C and a fronting edge portion 140 of electrode D. Similarly, in FIG. 4H, the potential is applied between electrodes D and E, forcing the near field 114 to be established between an edge portion 141 of electrode D, and a fronting edge portion 142 of elongate electrode E.

It is thus seen in FIGS. 4A–4H that through appropriate control of where the potential is applied relative to the electrodes A, B, C, D and E, it is possible to control the positioning of the near field 114 within the conductive media 108, and more particularly, it is seen that the near field 114 (and hence the location within the media 108 where stimulation occurs) can be selectively moved around within the conductive media as needed and/or desired. It is to be emphasized that only a portion of the possible electrode groupings are illustrated in FIGS. 4A–4H. Hence, the near field 114 could actually be moved around to many more locations than are shown in FIGS. 4A–4H. It is thus apparent that the near field 114 can actually be steered to almost any desired location within the conductive media 108, thereby allowing stimulation to also occur at such desired location.

Turning next to FIGS. 5 through 10B, there will be presented a description of an implantable intracochlear electrode array, sized and shaped for insertion into the cochlea of a human patient. Such an array is representative of one type of electrode array that may be made and used in accordance with the principles of the present invention. It is to be understood, however, that the present invention is not limited to just an intracochlear electrode array, but may be used for any FES or other application where an effective bipolar electrode array, or narrowly focused distribution(s) of electrical potentials, is/are needed.

Figure 5:
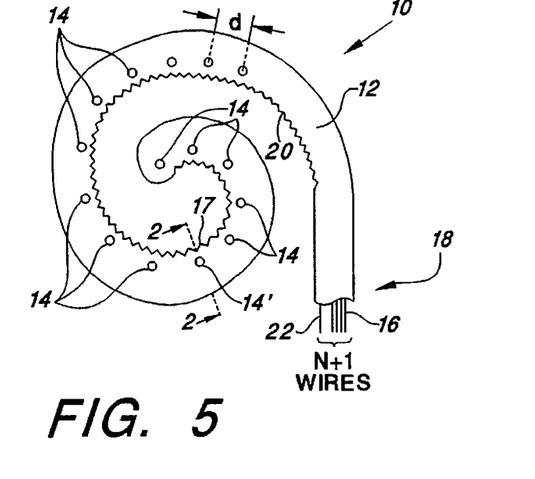
FIG. 5 is one embodiment of an electrode array made in accordance with the present invention, which array is especially adapted for insertion into the cochlea.
Figure 6:
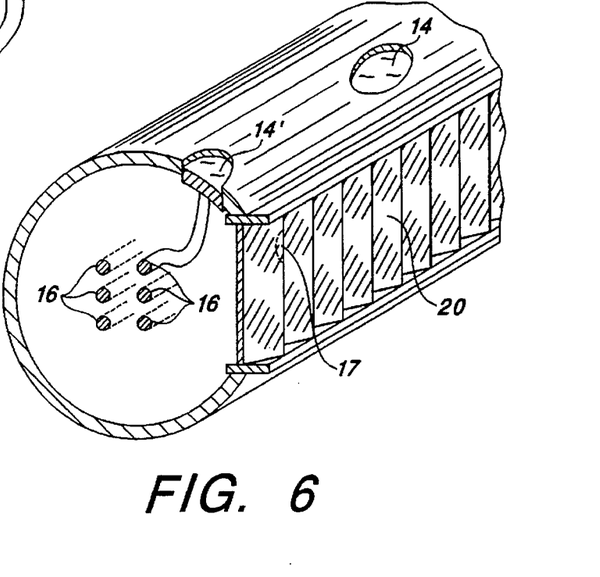
FIG. 6 is perspective sectional view taken generally at the line 2—2 of FIG. 5.

Referring then to FIGS. 5 and 6, there is shown an implantable electrode array 10 made in accordance with the present invention. FIG. 5 shows a plan view of the electrode. FIG. 6 depicts a cross-sectional/perspective view taken along the line 2—2 in FIG. 5. As seen in these figures, the electrode array 10 includes an elongate, non-conductive, flexible, resilient carrier 12 formed into a desired shape. The carrier may be formed, e.g., from silicone rubber. For insertion into the cochlea of a human ear, the desired shape is a spiral shape, as shown in FIG. 5. However, for other applications, any desired shape may be employed.

A multiplicity of N spaced-apart single electrodes 14 are formed on the carrier 12, each having a separate wire or conductor 16 connected thereto. The number of single electrodes N may vary, e.g., from 3 to 36, or more, depending upon the particular application for which the electrode will be used. Fifteen electrodes 14 are shown in FIG. 5 (which is typical for a cochlear electrode array). Each of the wires 16 is connected to a respective electrode 14. The wires 16 from all of the electrodes 14 pass through the carrier 12, as seen best in FIG. 6, to a proximal end 18 of the carrier, seen best in FIG. 5. At the proximal end 18, the respective wires 16 are accessible so that individual electrical contact may be made therewith.

An elongate common electrode 20 is formed along one side of the carrier 12. This elongate common electrode 20 has an additional wire 22 connected thereto that passes through the carrier 12 to its proximal end 18. Electrical contact may be thus be made with each of the electrodes 14 and the elongate common electrode 20 from the proximal end 18 of the array. Thus, it is seen that for N electrodes 14, there will be N+1 wires (or other conductors) exiting from the proximal end of the array 10 to facilitate electrical contact with each of the electrodes.

The elongate common electrode 20 may take numerous forms and shapes. Preferably, the electrode 20 is made from an appropriate resilient material having spring-like properties that impart the desired shape to the resilient carrier 12. Thus, as shown in the example of FIG. 5, the array 10 assumes a spiral shape, with the elongate electrode 20 being positioned on the inside curve of the spiral, and the electrodes 14 being positioned to lie close to, but not touching, the elongate electrode 20. Preferably, the electrodes 14 are equally spaced a distance "d" apart, where d may assume any preferred spacing, e.g., 0.5 to 10.0 mm. For a cochlear electrode, the spacing d is typically on the order of 0.8 to 1.2 mm, e.g., 1.0 mm. For some applications, the spacing between the point electrodes may vary.

Many of the details associated with fabricating an electrode array 10 as described herein are the same as is known in the art for making implantable leads and other devices for use with electro-biomedical systems. Reference is made, e.g., to Applicant Loeb's prior patent U.S. Pat. Nos. 4,686,765 and 4,819,647, both of which are incorporated herein by reference. Reference is also made to the large volume of art relating to the fabrication of implantable pacemaker leads.

Figure 7:
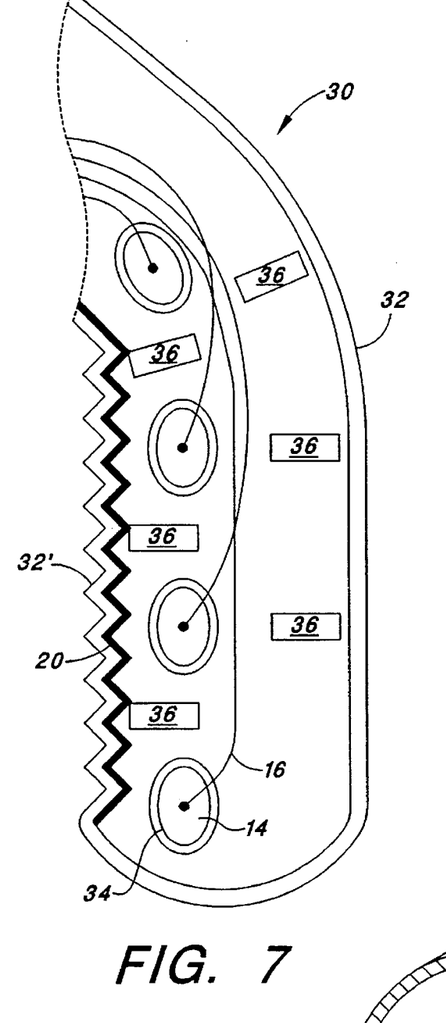
FIG. 7 shows a top view of a mold that may be used to make a cochlear electrode array of the type shown in FIG. 5.

Generally, the electrode array 10 is made using a mold as shown in FIG. 7, which figure shows a top view of a distal portion of the mold 30. The mold 30 has a wall 32 that defines the size and general shape of the electrode array 10. Recesses 34 are placed in the wall 32 at appropriate locations where the single electrodes 14 are to be positioned. Iridium metal electrodes 14 are then inserted into the recesses 34. Respective wires 16 are then bonded to each electrode 14, with the wires 16 being positioned more or less in the center of the mold 30. Rib alignment preforms 36 are judiciously spaced throughout the mold 30. The inside of the mold walls 32 are preferably coated with a material such as polyvinyl alcohol that adheres to and protects the electrode surface, and that can be subsequently removed from those surfaces so that the electrodes are exposed on the surface of the completed electrode array 10. An elongate strip of iridium is formed and bent to fit against the mold wall 32' in the region where the wall is corrugated. A suitable connection wire 22 (not shown in FIG. 7) is then attached to the strip 20 at an appropriate location. Typically, as shown in FIG. 7, such strip is folded to have a plurality of accordion-like folds between each point electrode 14, although such folding is not required. Advantageously, such folds facilitate the bending of the electrode array once it has been fabricated, yet when thus formed and folded, the electrode strip 20 exhibits spring-like properties that tend to pull it back to its original shape when bent. Note, that for cochlear stimulation applications, where the electrode array 10 assumes the general shape of a spiral (to match the spiral shape of the cochlea, but with a somewhat tighter pitch than that of the cochlea), it is preferred that the elongate electrode 20 be positioned along the inside edge of the spiral, as shown in FIG. 5.

With all the components positioned within the mold 30, the carrier 12 is formed by injecting the carrier material, e.g., silicone elastomer, in liquid form, within the mold, and then curing the material through the appropriate application of heat, as is known in the art. After removal from the mode, any polyvinyl alcohol remaining on the surfaces of the iridium contacts is washed off with hot water. The various iridium contacts are electrochemically activated to the extent desired by applying appropriate voltage excursions in an electrolytic bath as is known in the art.

A preferred electrode array 10 made for insertion into an adult human cochlea in accordance with the present invention is approximately 25 mm long, 1 mm in diameter, has 16 point electrodes, and is shaped in a spiral or coil to have approximately 1½ turns. The point electrodes 14 are each made from activated iridium and are about 0.3 mm in diameter, and are spaced approximately 1 mm apart. The elongate common electrode 20 is also made from a strip of activated iridium that is approximately 0.2 mm wide and 15 mm long. The carrier 12 is made from silicone elastomer. The wires 16 and 22 that connect to the electrodes 14 and 20 are platinum-10% iridium alloy, 37 μm in diameter. Advantageously, all of the above materials are biocompatible and sterilizable by various conventional means, and may thus be safely implanted within a human or other animal.

In use, an electric potential is applied between a selected one of the wires 16 and the wire 22 at the proximal end of the carrier 12, thereby applying the electric potential between a selected one of the multiplicity of electrodes 14 and the common electrode 20. Such electric potential creates a spatial distribution of electrical fields that, when the electrode array 10 is inserted into a volume-conductive media, e.g., within the cochlea, causes an electrical stimulating current to flow through the media between the selected electrode and a small area of the elongate common electrode 20 adjacent the selected single electrode. For example, if the electric potential is applied between the electrode 14' and the common electrode 20, then the stimulating current flows in the conductive media between the point electrode 14' and a small area 17 on the elongate common electrode 20 adjacent the point electrode 14'. Such electrical stimulating current effectively provides a bipolar stimulation between the selected single electrode and the small area of the elongate common electrode adjacent thereto. Thus, it is seen that a multiplicity of bipolar electrode sites are provided through selective application of an electric potential to appropriate ones of the wires 16 and the wire 22. In actual practice, as explained below, each current pulse depicted as a simple square pulse in FIGS. 9B and 10B would more commonly be a biphasic pulse with equal but opposite amounts of charge flowing in its two phases.

Getting the stimulation current to flow between the selected single electrode 14 and a small area adjacent thereto on the elongate common electrode 20 requires that the lowest impedance path through the conductive media be between the point electrode and the closest point on the common electrode. Such is accomplished with the electrode array 10 of the present invention through the careful selection of the array's geometry and electrode materials.

Significantly, it has been discovered (through systematic recording of the spatial distribution of electrical fields surrounding the electrodes 14 and electrode 20) that the electrode configuration shown in FIGS. 5 and 6 produces a dipole gradient typical of a bipolar pair of small closely-spaced contacts. That is, application of an electrical potential between one of the small single electrodes 14, e.g., the electrode 14', and the elongate electrode 20, produces an effective electrical field dipole gradient between the small electrode 14' and a small region 17 on the surface of the elongate electrode 20 immediately adjacent to the nearby electrode 14'. As a consequence, almost all of the stimulating current flow through the interface occurs at the activated electrode 14' and the adjacent region 17, just as though the electrode 14' and the region 17 comprised a bipolar pair composed from the point electrodes.

As used herein, the phrase "immediately adjacent to" refers to the shortest electrical distance between the activated single electrode 14 and the elongate electrode 20. If it is assumed that the volume conductive media wherein the electrode array 10 is inserted presents a uniform resistance, then "immediately adjacent to" also refers to the shortest lineal distance between the activated point electrode 14 and the elongate electrode 20. For the type of elongate electrode 20 shown in FIG. 6, comprising a strip of activated iridium metal that is folded with a series of accordion folds, the point 17 on the surface of the elongate electrode 20 that is immediately adjacent to the activated electrode 14' will typically lie on a ridge of the fold nearest the activated single electrode 14'.

Figure 8:
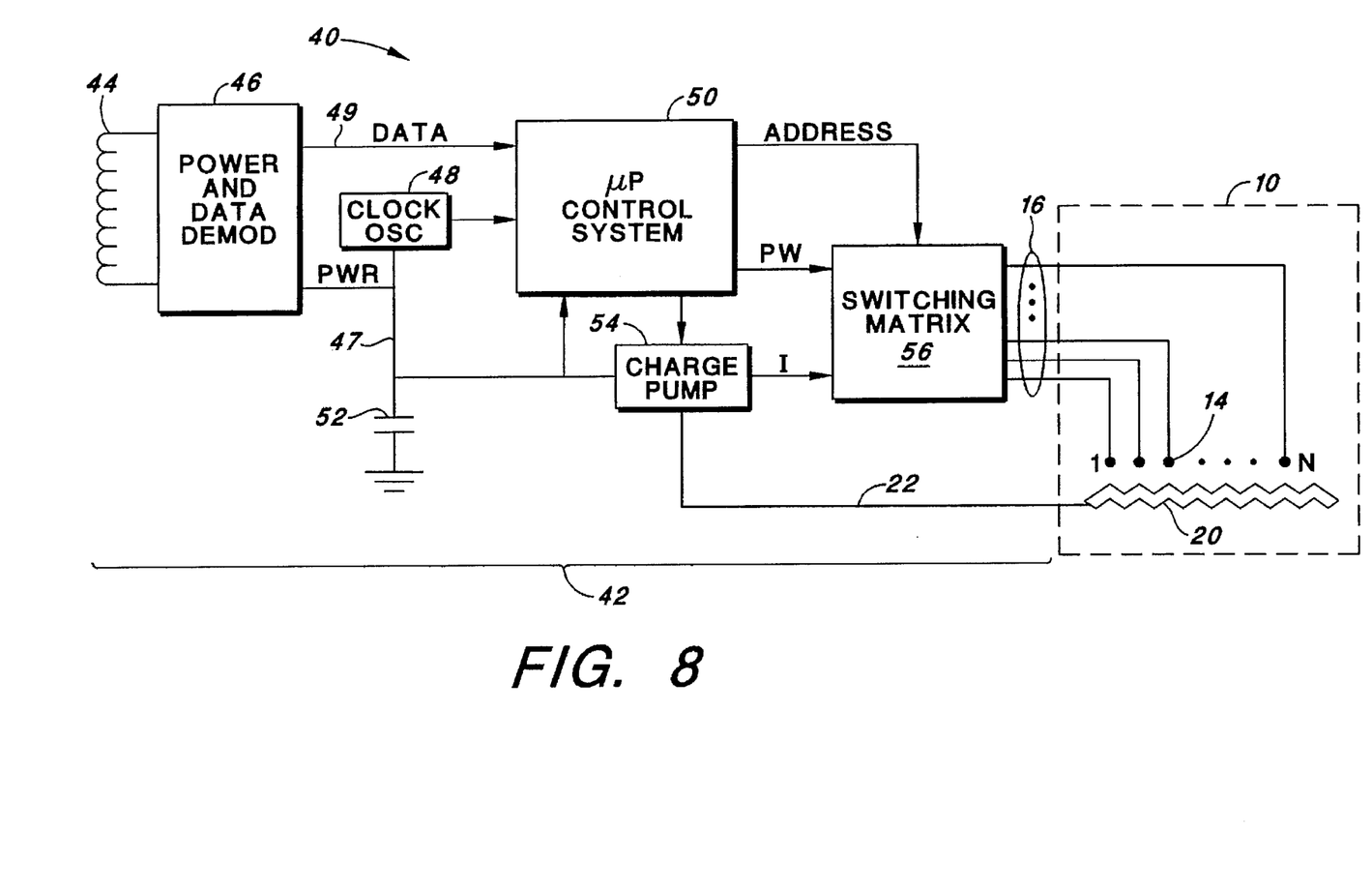
FIG. 8 is a functional electrical schematic diagram of an implantable stimulator that may be used with the cochlear electrode array of FIG. 3 or FIG. 5.

FIG. 8 is a functional electrical schematic diagram of an implantable stimulator 40 that may be used with the electrode array 10 of the present invention. Together, the stimulator 40 and electrode array 10 comprise a functional electrical stimulation (FES) system. The electrode array 10 includes a single, elongate electrode contact 20 and N individual electrode contacts 14, labeled 1 through N, that are spaced apart from each other and from the elongate electrode contact. For most FES applications, N is at least three, and will most often be much greater than three, e.g., 8 to 32. As described above, the electrode array 10 is adapted to be positioned within volume-conductive media.

The electrode array 10 is connected, by way of connection wires 16 and 22, to appropriate electrical circuitry 42 that selectively applies a pulsed electrical potential between the elongate electrode contact 20 and at least one of the N individual electrode contacts 14. Such applied electrical potential establishes a gradient electric field through the volume-conductive media, which gradient field, in turn, causes an electrical current (current density) to flow in the volume-conductive media between the at least one individual electrode contact 14 and a small portion of the elongate electrode contact 20 immediately adjacent to the contact 14. This electrical current thus achieves the same stimulation effect as would be achieved by bipolar electrodes located in the same position as the activated individual electrode contact 14 and the small portion of the elongate electrode contact 20.

As seen in FIG. 8, the electrical circuitry 42 includes a receiving coil 44 coupled to a power and data demodulation circuit 46. In operation, the coil 44 is inductively coupled to an external coil, not shown, and a modulated carrier signal is induced into the coil 44. The power and data demodulation circuit 46 then demodulates the induced signal, separates power from data, and provides a power (operating voltage) signal on signal line 47, and a data signal on signal line 49. Power from the power signal line 47 is stored in a capacitor 52, and the power signal line provides operating power to the remaining circuits of the stimulation system.

The data signal line is applied to a microprocessor 50, or equivalent control circuit. The received data specifies the "address" (i.e., which of the N electrodes is to receive a pulse) where a stimulation pulse is to be applied, along with how much energy the stimulation pulse is to have. The stimulation energy may be controlled either by controlling the duration (width) of the stimulation pulse and/or the amplitude of the stimulation pulse. A clock oscillator circuit 48 provides a timing (clock) signal to the processor 50. A charge pump circuit 54 multiplies the stored voltage held on the capacitor 52 by a prescribed amount in order to achieve whatever amplitude may be needed to create a stimulation pulse of the desired amplitude. Such stimulation pulse is then applied to the addressed stimulation electrode (i.e., one of the N stimulation electrodes 14) for a specified time (pulse width) through a suitable switching matrix 56. The stimulation current thus flows from the charge pump circuit 54, through the switching matrix 56, through one of the wires 16 to the addressed electrode 14, through the conductive media to a point on the elongate electrode 20, and returns to the charge pump circuit 54 through the wire 22.

The circuitry shown in FIG. 8 may take numerous forms, and may be implemented using many different types of technology, e.g., CMOS integrated circuits, and stimulation strategies. Representative circuits that achieve the function shown in FIG. 8 may be found, for example, in U.S. Pat. Nos. 3,752,939; 4,532,930; 4,918,745; 4,931,795; 4,990,845; and U.S. patent application Ser. No. 08/023,584, filed Feb. 26, 1993, all of which patents and patent applications are incorporated herein by reference.

Figure 9A:
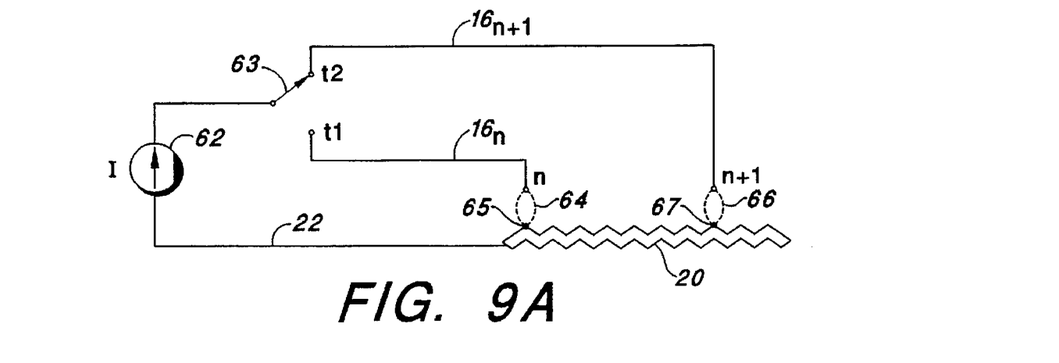
FIG. 9A is an electrical schematic diagram that generally illustrates the bipolar effect achievable when an elongate electrode is used in combination with a plurality of other adjacent electrodes.
Figure 9B:
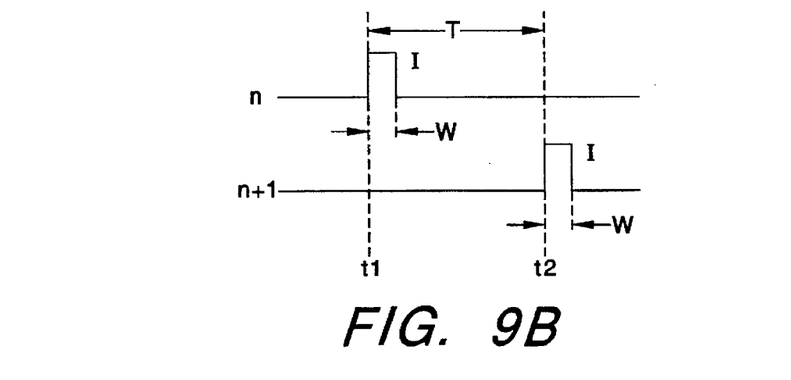
FIG. 9B is a timing diagram associated with one mode of operation of the circuit of FIG. 9A.

FIG. 9A is an electrical schematic diagram that illustrates the bipolar effect achieved by the electrode array of FIG. 5 when respective point electrodes are pulsed at different times with current pulses. FIG. 9B is a timing diagram associated with the operation of the circuit of FIG. 9B. In FIG. 9A, a current source 62 and switch 63 represent the function carried out by the electronic circuitry 42 of FIG. 8. A current pulse of amplitude I and width W is applied to the $n^{th}$ electrode at time t1 and to the $(n+1)^{th}$ electrode at time t2, where both the $n^{th}$ and $(n+1)^{th}$ electrodes are respective ones of the N electrodes 14 included within the electrode array 10. Respective wires $16_n$ and $16_{n+1}$ connect the switch 63 to the electrodes. During the duration of the applied pulse, at either time t1 or t2, a dipole electric field (represented by the dotted lines 64 and 66) is created between the selected $n^{th}$ and $(n+1)^{th}$ electrodes and the elongate common electrode 20. When volume-conductive media, e.g., body tissue, surrounds the electrodes, such dipole electric field causes the current pulse I to flow through the conductive media, with an electrical return path through the wire 22. In actual practice, each current pulse depicted as a simple square pulse in FIGS. 9B and 10B would more commonly be a biphasic pulse with equal but opposite amounts of charge flowing in its 2 phases.

Advantageously, by positioning the N electrodes along the course of the elongate electrode 20, it is possible to create N perpendicular bipolar fields using N+1 leads (wires) instead of the 2N leads typically required by discrete pairs of bipolar electrodes. Furthermore, it is possible to influence the steepness of the electric field gradient along the length of the longitudinal axis of the electrode by simply changing the frequency content of the stimulating waveform (e.g., by changing the shape of the stimulation pulse without significantly changing the stimulation energy through either increasing the pulse amplitude and decreasing pulse width, or decreasing pulse amplitude and increasing pulse width). When the relative frequency content of the stimulation pulse is high (which occurs with short, or narrow, pulses, e.g., on the order of 100 μs or less depending on the surface roughness and degree of activation of the contact material), the density of current flow in the media surrounding the contacts is determined primarily by the shortest paths available between the electrode contacts, which are the paths between the most closely approximated edges of the small single electrode contacts 14 and the adjacent portion of the elongated contact 20. When the relative frequency content of the stimulation pulse is low (which occurs with long, or wide, pulses, on the order of 200 μs or more), the capacitive component of the interfacial impedance causes it to dominate the effective impedance of the circuit, thereby distributing the current density more uniformly along the extent of both the single contacts 14 and the elongate contact 20. As the frequency content becomes lower and lower, the situation approaches that of a monopolar configuration, where the proximity of the elongated contact contributes little to the distribution of the resultant electric fields.

In practice, that which is shown in FIGS. 9A and 9B is greatly simplified over the types of stimulation pulse and pulse patterns that may be achieved with an electrode 10 made in accordance with the present invention. For example, the stimulation pulse may be a biphasic stimulation pulse, rather than a monopolar stimulation pulse as shown in FIG. 9B. A biphasic stimulation pulse is a pulse of one polarity followed immediately (or very soon) thereafter with another pulse of the opposite polarity. For some FES applications, biphasic stimulation pulses are preferred. Further, the N electrodes need not be stimulated in any fixed sequence, as might be suggested by FIG. 9A [where the $(n+1)^{th}$ electrode is stimulated immediately following stimulation of the $n^{th}$ electrode]. Rather, the electrodes may be stimulated in any prescribed sequence, or even in a random sequence, as best suits the needs of the particular patient. In addition, the rate at which the stimulation pulses are applied, i.e., the reciprocal of the period T between the applied pulses, may be adjusted to suit the particular FES application at hand. For certain cochlear stimulation applications, for example, the inter-pulse period T may vary from 1 to 1000 μs.

That which is illustrated in FIGS. 9A and 9B above assumes that only one of the single electrodes 14 is activated (has an electric potential or current source applied thereto) at any given time. One of the advantages of using the electrode array herein described is that the geometry of the array can be used to create an arbitrary number of "virtual dipoles" that are oriented perpendicularly to the elongate electrode 20, but which are located in positions that are intermediate between the positions of the available point electrodes 14. Such "virtual dipoles" are created by activating more than one of the point electrodes 14 at the same time.

Figure 10A:
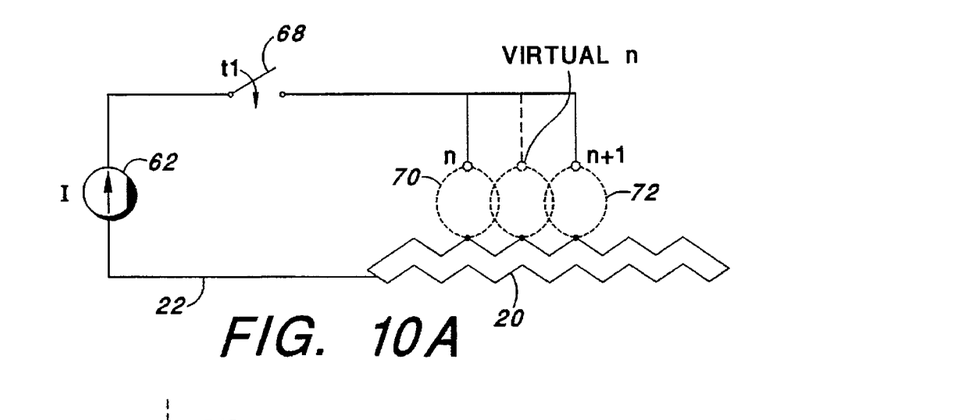
FIG. 10A is an electrical schematic diagram that illustrates the creation of a virtual electrode achieved by simultaneously pulsing more than one electrode of an electrode array of the type shown in FIG. 9A.
Figure 10B:
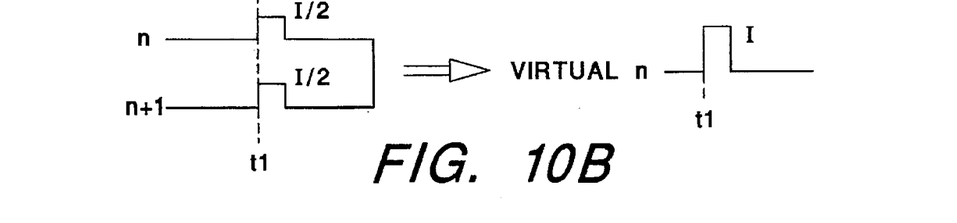
FIG. 10B is a timing diagram associated with one mode of operation of the circuit of FIG. 10A.

The creation of a virtual dipole is illustrated in FIGS. 10A and 10B. FIG. 10A is an electrical schematic diagram that illustrates the creation of a virtual point electrode achieved by simultaneously pulsing more than one point electrode of the electrode array. FIG. 10B is a timing diagram associated with the operation of the circuit of FIG. 10A. In FIG. 10A, a current source 62 applies a current I to both an $n^{th}$ and an $(n+1)^{th}$ electrode of the N electrodes 14 at the same time, time t1, through closure of switch 68. Each electrode, if activated alone, would thus create a respective dipole field 70, 72 that would inject the current I into the surrounding media. However, when both electrodes are activated simultaneously, each injects a portion of the total current I into the conductive media surrounding the electrodes, with the total current I returning to the current source 62 via the elongate electrode 20 and the wire 22. The fields 70, 72, that would be produced by each single electrode alone combine linearly to produce a net dipole 74 that appears be to located intermediate the $n^{th}$ and the $(n+1)^{th}$ electrodes. Such net dipole 74 is, like the field 70, directed perpendicularly away from the long axis of the elongate electrode 20.

When only two adjacent electrodes are activated at the same time, as shown in FIG. 10A, then the virtual dipole is positioned effectively mid-way between the two activated electrodes. The position of the virtual dipole may be electronically controlled, as desired, by activating more than two electrodes at the same time, e.g., by activating three electrodes, or any other combination of electrodes (whether adjacent or not). Further, the position of the virtual dipole may be controlled by limiting the amount of current supplied to each of the activated electrodes, e.g., with one electrode receiving ⅓ of the current, and the other electrode receiving ⅔ of the current. Through such controls, a large number of virtual dipoles may thus be created at multiple positions as best meets the needs for the particular patient and FES application at hand.

Significantly, the electrode array described herein can produce a wide range of desirable fields, and is particularly suited for a cochlear electrode because the arrangement of electrodes and leads is mechanically sound for manufacture and handling. The electrode array, for example, exhibits desirable surgical handling properties in that it can be easily sterilized, straightened, and then inserted into the spiral-shaped cochlea. Once inserted, the elongate electrode and elastomeric carrier pull the electrode back to its desired spiral shape so that the elongate electrode hugs the medial wall of the cochlea spiral, thereby bringing the point electrodes into proper proximity to the neurons that need to be stimulated.

As described above, it is thus seen that the invention provides edge effect electrodes that may be used to direct stimulation currents to desired locations within conductive media.

It is further seen that one embodiment of the invention provides a passive implantable electrode array for use in FES or other applications that effectively provides bipolar stimulation for N narrowly focussed stimulation sites, while only requiring N+1 electrical leads connected thereto. As a result, such electrode array is small, flexible and compact, and is particularly suited for implantation in very tight quarters or small volumes, such as within the cochlea.

As further described above, it is seen that the electrode array provides a geometry that permits the gradients of the stimulation current density to be controllable, in part, by electronic means, and in part by the geometry of the array and the materials from which the electrodes of the array are made.

While the invention herein disclosed has been described by means of specific embodiments and applications thereof, numerous modifications and variations could be made thereto by those skilled in the art without departing from the scope of the invention set forth in the claims.

What is claimed is:

1. A functional electrical stimulation (FES) system comprising:
   an electrode array comprising:
   a flexible carrier,
   a single, elongate electrode contact positioned on said carrier, and
   a multiplicity of individual electrode contacts that are spaced apart from each other a distance d on said carrier, where d is less than about 1.2 mm, said individual electrode contacts also being spaced apart from said elongate electrode contact,
   said carrier having a general spiral shape, thereby forming a spiral-shaped electrode array, the elongate electrode contact being positioned on the carrier so that it lies along an inside edge of the spiral-shaped electrode array, said electrode array being positionable within volume-conductive media of a cochlea of a human ear; and means for selectively applying a pulsed electrical current between said elongate electrode contact and at least one of said multiplicity of individual electrode contacts so as to create a gradient field through the volume-conductive media, said gradient field creating a current density in the volume-conductive media, elongate electrode contact, and at least one individual electrode contact, said current density appearing as a bipolar stimulation between the at least one individual electrode contact and a small portion of the elongate electrode contact adjacent the at least one individual electrode contact;

said means for selectively applying a pulsed electrical current comprising an implantable cochlear stimulator that includes power/data receiving means for receiving power and data from a non-implanted transmitter, and stimulation control means for applying the received power as an electric potential between selected ones of said multiplicity of individual electrode contacts and said elongate common electrode contact as controlled by the received data, thereby selectively creating the gradient field through the volume-conductive media as controlled by the received data.

2. The FES system as set forth in claim 1 wherein said elongate electrode contact is made from a material having spring-like properties that help maintain the spiral shape of said electrode array.

3. The FES system as set forth in claim 1 wherein at least one of said multiplicity of individual electrode contacts and said elongate common electrode contact have surfaces comprising activated iridium, thereby reducing interfacial impedance of the electrode contacts when interfaced with volume-conductive media.

4. The FES system as set forth in claim 1 wherein all of said multiplicity of individual electrode contacts and said elongate electrode contact have surfaces comprising activated iridium.

5. The FES system as set forth in claim 1 wherein the stimulation control means of the implantable cochlear stimulator includes means for applying the pulsed electrical current between the elongate electrode contact and a selected one of the individual electrode contacts at one instant of time, and for rapidly selecting others of the individual electrode contacts in a prescribed sequence at other instants of time, whereby the pulsed electrical current is never applied to more than one of the individual electrode contacts at the same time.

6. The FES system as set forth in claim 1 wherein the stimulation control means of the implantable cochlear stimulator includes means for simultaneously applying the pulsed electrical current between the elongate electrode contact and a selected plurality of the individual electrode contacts, whereby the gradient field created in the volume-conductive media is shaped by the pulsed electrical current applied to the selected plurality of individual electrode contacts and the spacing of the individual electrode contacts so as to create a virtual electrode contact in a region intermediate the selected plurality of individual electrode contacts to which the pulsed electrical current is applied.

7. An electrode system for providing electrical stimulation to a desired location within volume-conductive media, comprising:

an implantable electrode array comprising a plurality of closely spaced metal contacts separated by less than about 10 mm, at least one of said metal contacts being coated with a coating of activated iridium, each metal contact having means for making electrical contact therewith, and each having a sufficient area to not function as a point source;

anti-corrosion means for preventing each of said metal contacts from corroding in the presence of a high current density at an edge of said metal contacts; and means for inducing an electric field between a pair of said plurality of metal contacts so that, when volume-conductive media is inserted therebetween, a high density electrical current flows from a portion of an edge of one of said metal contacts of said pair through the volume-conductive media to the other metal contact of said pair, whereby an edge-effect electrical current flow is induced between the pair of metal contacts.

8. The electrode system of claim 7 wherein the anti-corrosion means further includes means for reducing the interfacial impedance of the metal contacts of the electrode array when interfaced with the volume-conductive media.

9. The electrode system as set forth in claim 7 wherein said anti-corrosion means comprises a coating of an oxide of tantalum metal placed on at least one of said metal contacts of said array.

10. The electrode system of claim 7 further including means for controlling the induced electric field so that the edge-effect electrical current flow is directed to a desired region within the volume-conductive media; whereby edge-effect electrical currents are used beneficially in a closely spaced bipolar metal contact configuration.

11. The electrode system of claim 10 wherein the means for controlling the induced electric field comprises means for applying a pulsed electric potential between a selected pair of said plurality of metal contacts, and means for adjusting a pulse width of said pulsed electric potential.

12. The electrode system of claim 11 wherein said electrode array includes:

at least one elongate metal contact, a plurality of smaller metal contacts, and a non-conductive carrier that holds said elongate metal contact in a fixed spaced-apart relationship relative to the plurality of smaller metal contacts, and wherein corresponding portions of each of the plurality of smaller metal contacts are approximately equidistant from an edge of said elongate metal contact, and further wherein said means for controlling the induced electric field so that the edge-effect electrical current flow is directed to a desired region within the volume-conductive media comprises means for selectively energizing a first pair of said plurality of metal contacts with an electric potential for a first pulsed time period, energizing a second pair of said metal contacts with an electric potential for a second pulsed time period, and continuing to energize a respective pair of said metal contacts with an electric potential for a specified pulsed time period, in a defined sequence, with only one pair of metal contacts being energized with an electric potential at any given instant of time, and wherein one of the metal contacts of each pair of metal contacts thus energized comprises the elongate metal contact, and wherein the direction of the current flow into a desired region of the volume-conductive media is a function of the pulsed time period of the electric potential applied to a given pair of metal contacts and the defined sequence in which the pairs of metal contacts are energized.

13. The electrode system of claim 12 wherein said non-conductive carrier has a spiral shape having an inside edge, and wherein said elongate metal contact lies on the inside edge of the spiral-shaped carrier.

14. An implantable electrode array comprising:
   an elongate, non-conductive, flexible, resilient carrier formed into a desired shape;
   a multiplicity of spaced-apart small electrodes formed on said carrier, each having a separate wire connected thereto, the wires from all of said small electrodes passing through said carrier to a proximal end thereof whereat electrical contact may be selectively made with each of said wires; and
   an elongate common electrode formed along one side of said carrier, said elongate common electrode having an additional wire connected thereto that passes through said carrier to its proximal end whereat electrical contact may be made therewith, said elongate common electrode having folds to provide a plurality of high points and low points along its length between adjacent ones of said small electrodes;
   whereby an electrical potential may be selectively applied between a selected one of said multiplicity of small electrodes and said common electrode by selectively applying the electrical potential to appropriate wires at the proximal end of said carrier, said electrical potential creating a spatial distribution of electrical fields that, when the electrode array is inserted into a volume-conductive media, causes an electrical stimulating current to flow through the media between the selected small electrode and a small area of the elongate common electrode adjacent the selected small electrode, thereby effectively providing bipolar stimulation between the selected small electrode and the small area of the elongate common electrode adjacent thereto, and
   whereby a multiplicity of bipolar electrode sites may be provided through selective application of a voltage potential to appropriate ones of said wires.

15. The electrode array as set forth in claim 14 wherein at least one of said multiplicity of small electrodes and said elongate common electrode have surfaces coated with activated iridium, thereby reducing interfacial impedance of the electrodes when interfaced with volume-conductive media.

16. The electrode array as set forth in claim 15 wherein all of said multiplicity of small electrodes and said elongate common electrode have surfaces comprising activated iridium.

17. The electrode array as set forth in claim 14 wherein said multiplicity of small electrodes are spaced apart a distance d on said carrier, where d is less than about 1.2 mm.

18. The electrode array as set forth in claim 14 wherein there are at least fifteen small electrodes formed on said carrier.

19. An electrode system for providing electrical stimulation to a desired location within volume-conductive media, comprising:
   an implantable electrode array comprising
      at least one elongate metal contact,
      a plurality of smaller metal contacts, and
      a non-conductive carrier that holds said elongate metal contact in a fixed spaced-apart relationship relative to the plurality of smaller metal contacts, said non-conductive carrier having a spiral shape having an inside edge, and
      wherein corresponding portions of each of the plurality of smaller metal contacts are approximately equidistant from an edge of said elongate metal contact, and further wherein said elongate metal contact lies on the inside edge of the spiral-shaped non-conductive carrier;
   means for inducing an electric field between a pair of metal contacts that includes said at least one elongate metal contact and a selected one of the plurality of smaller metal contacts so that, when volume-conductive media is inserted between the pair of metal contacts, a high density electrical current flows from a portion of an edge of said elongate metal contact through the volume-conductive media to the smaller metal contact of said pair, whereby an edge-effect electrical current flow is induced between the pair of metal contacts; and
   means for controlling the induced electric field so that the edge-effect electrical current flow is directed to a desired region within the volume-conductive media, said means for controlling the induced electric field comprising means for selectively energizing a respective pair of said metal contacts with an electric potential for a specified pulsed time period in a defined sequence, with only one pair of metal contacts being energized with an electric potential at any given instant of time, and wherein the direction of the current flow into a desired region of the volume-conductive media is a function of the pulsed time period of the electric potential applied to a given pair of metal contacts and the defined sequence in which the respective pairs of metal contacts are energized, whereby edge-effect electrical currents are used beneficially in a closely spaced bipolar metal contact configuration.

20. An implantable electrode array comprising:
   a elongate, non-conductive, flexible, resilient carrier formed into a desired shape;
   a multiplicity of spaced-apart small electrodes formed on said carrier, each having a separate wire connected thereto, the wires from all of said small electrodes passing through said carrier to a proximal end thereof whereat electrical contact may be selectively made with each of said wires; and
   an elongate common electrode formed along one side of said carrier, said elongate common electrode having spring-like properties that impart the desired shape to said resilient carrier, said elongate common electrode further having an additional wire connected thereto that passes through said carrier to its proximal end whereat electrical contact may be made therewith;
   whereby an electrical potential may be selectively applied between a selected one of said multiplicity of small electrodes and said common electrode by selectively applying the electrical potential to appropriate wires at the proximal end of said carrier, said electrical potential creating a spatial distribution of electrical fields that, when the electrode array is inserted into a volume-conductive media, causes an electrical stimulating current to flow through the media between the selected small electrode and a small area of the elongate common electrode adjacent the selected small electrode, thereby effectively providing bipolar stimulation between the selected small electrode and the small area of the elongate common electrode adjacent thereto, and
   whereby a multiplicity of bipolar electrode sites may be provided through selective application of a voltage potential to appropriate ones of said wires.

21. An implantable cochlear electrode array comprising:
   a elongate, non-conductive, flexible, resilient spiral-shaped carrier formed to fit within a cochlea of a human ear;

a multiplicity of spaced-apart small electrodes formed on said carrier, each having a separate wire connected thereto, the wires from all of said small electrodes passing through said carrier to a proximal end thereof whereat electrical contact may be selectively made with each of said wires, and wherein said multiplicity of small electrodes are spaced apart a distance d on said carrier, where d is less than about 1.2 mm; and an elongate common electrode formed along one side of said carrier, said elongate common electrode having an additional wire connected thereto that passes through said carrier to its proximal end whereat electrical contact may be made therewith;

whereby an electrical potential may be selectively applied between a selected one of said multiplicity of small electrodes and said common electrode by selectively applying the electrical potential to appropriate wires at the proximal end of said carrier, said electrical potential creating a spatial distribution of electrical fields that, when the electrode array is inserted into a volume-conductive media, causes an electrical stimulating current to flow through the media between the selected small electrode and a small area of the elongate common electrode adjacent the selected small electrode, thereby effectively providing bipolar stimulation between the selected small electrode and the small area of the elongate common electrode adjacent thereto, and whereby a multiplicity of bipolar electrode sites may be provided through selective application of a voltage potential to appropriate ones of said wires.

22. The electrode array as set forth in claim 21 wherein the elongate common electrode is positioned on the spiral-shaped carrier so that it lies along an inside edge of the spiral-shaped carrier.

* * * * *